United States Patent
Matsushima et al.

(10) Patent No.: US 9,607,368 B2
(45) Date of Patent: Mar. 28, 2017

(54) GRAIN APPEARANCE MEASURING APPARATUS

(71) Applicant: SATAKE CORPORATION, Tokyo (JP)

(72) Inventors: Hideaki Matsushima, Hiroshima (JP); Hiroki Ishizuki, Hiroshima (JP); Hiroaki Takeuchi, Hiroshima (JP)

(73) Assignee: Satake Corporation (JP)

( * ) Notice: Subject to any disclaimer, the term of this patent is extended or adjusted under 35 U.S.C. 154(b) by 121 days.

(21) Appl. No.: 14/411,099

(22) PCT Filed: May 16, 2013

(86) PCT No.: PCT/JP2013/063700
§ 371 (c)(1),
(2) Date: Dec. 24, 2014

(87) PCT Pub. No.: WO2014/002636
PCT Pub. Date: Jan. 3, 2014

(65) Prior Publication Data
US 2015/0146938 A1 May 28, 2015

(30) Foreign Application Priority Data
Jun. 27, 2012 (JP) ................................ 2012-143709

(51) Int. Cl.
*G06K 9/00* (2006.01)
*G06T 7/00* (2017.01)
(Continued)

(52) U.S. Cl.
CPC ........... *G06T 7/0004* (2013.01); *G01N 21/85* (2013.01); *G06T 11/60* (2013.01); *G06T 2207/20221* (2013.01); *G06T 2207/30128* (2013.01)

(58) Field of Classification Search
CPC ............. G06K 9/00; G06T 7/00; G01N 21/00
(Continued)

(56) References Cited

U.S. PATENT DOCUMENTS 4,713,781 A * 12/1987 Brizgis .............. G01N 21/6456
250/222.2
5,917,927 A * 6/1999 Satake .................. G06T 7/0004
356/237.1
(Continued)

FOREIGN PATENT DOCUMENTS

CN 1271857 A 11/2000
CN 101109743 A 1/2008
(Continued)

OTHER PUBLICATIONS

International Search Report for PCT/JP2013/063700 dated Jul. 9, 2013.
(Continued)

*Primary Examiner* — Abolfazl Tabatabai
(74) *Attorney, Agent, or Firm* — Lerner, David, Littenberg, Krumholz & Mentlik, LLP (57) ABSTRACT

A technical object is to enable optical checks to be performed while allowing visual checks using a sample pan to be performed in a pseudo manner using an aggregate image (pseudo image) depicting grains loaded on the sample pan, by optically checking the grains using image information on the grains imaged by an imaging apparatus and creating the aggregate image using the image information. Thus, a grain appearance measuring apparatus includes imaging means for imaging a plurality of grains, analysis means for analyzing image information on the grains imaged by the imaging means in units of grains, processing means for processing the image information to form an aggregate image of the grains, and means for saving and/or displaying the aggregate image processed by the processing means. The processing means extracts grain images from the image
(Continued)

information in units of grains and arranges the extracted grain images in units of grains, in a close state where the grain images are close to one another to form an aggregate image of the grain images.

5 Claims, 6 Drawing Sheets

(51) Int. Cl.
  *G01N 21/85* (2006.01)
  *G06T 11/60* (2006.01)
  *G03C 8/00* (2006.01)
(58) Field of Classification Search
  USPC .......................................................... 382/110
  See application file for complete search history.

(56) References Cited

U.S. PATENT DOCUMENTS

| | | | | |
|---|---|---|---|---|
| 7,058,335 B2 * | 6/2006 | Sugiura | ............. | G03G 21/0058 399/100 |
| 2013/0051622 A1 | 2/2013 | Ishizuki et al. | | |

FOREIGN PATENT DOCUMENTS

| | | | |
|---|---|---|---|
| CN | 101281112 | A | 10/2008 |
| CN | 101788497 | A | 7/2010 |
| CN | 201699810 | U | 1/2011 |
| EP | 1046902 | A2 | 10/2000 |
| EP | 1518652 | A1 | 3/2005 |
| JP | H10-104165 | A | 4/1998 |
| JP | 2001-041895 | A | 2/2001 |
| JP | 2003-319165 | A | 11/2003 |
| JP | 2004-361333 | A | 12/2004 |
| JP | 2006-071552 | A | 3/2006 |
| JP | 2006200945 | A | 8/2006 |
| JP | 2009-002844 | A | 1/2009 |
| JP | 4716389 | B | 10/2011 |
| JP | 2011242284 | A | 12/2011 |
| WO | 2011145287 | A1 | 11/2011 |

OTHER PUBLICATIONS

Extended European Search Report for Application No. 13809865.2 dated Jan. 19, 2016.

* cited by examiner

GRAIN APPEARANCE MEASURING APPARATUS

TECHNICAL FIELD

The present invention relates to a grain appearance measuring apparatus including means for creating, saving, and/or displaying an aggregate image (pseudo image) of grains loaded on a sample pan, using image information on a plurality of grains imaged for measurement.

BACKGROUND ART

Figure 12:
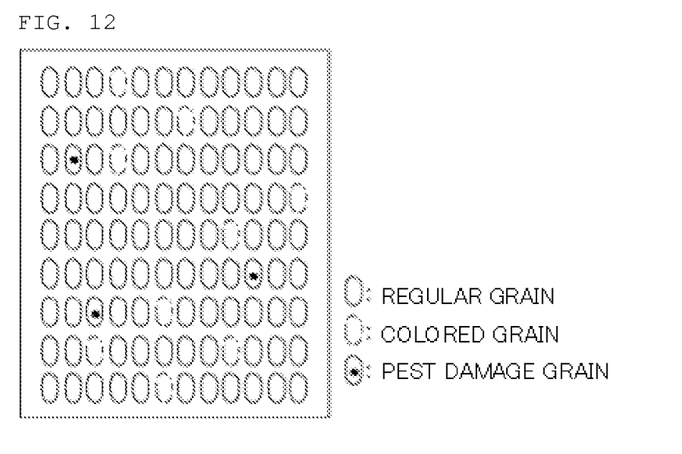
FIG. 12 is an aggregate image of arrayed grains resulting from processing of image information on grains imaged by a conventional grain appearance measuring apparatus.

Conventionally, grains are imaged using an imaging apparatus such as a scanner, and sorted using image information obtained by imaging. Patent document 1 describes that grains are extracted one by one from the image information resulting from the imaging of the grains, the extracted grains are sorted in units of grains, and the results of the sorting are displayed such that the grains are brought into lines in units of grains. This display method allows the sorted grains to be displayed as depicted in FIG. 12.

Even now, grains are visually checked. The visual check is performed using a sample pan called a carton such as that described in Patent document 2. The visual check using the sample pan is appreciated in that the check enables rough sorting at first sight using the grains loaded on the sample pan.

There has been a desire that, even when the check is performed using such optical means as described in Patent document 1, an image can be saved and displayed which depicts that the sample grains used for the check have been loaded on the sample pan.

However, much time and effort are needed to load, on the sample pan, the sample grains imaged by the imaging apparatus such as a scanner and then to image the sample pan with the sample grains loaded thereon using imaging means (a digital camera or the like) different from the above-described imaging apparatus. Furthermore, these pieces of image information need to be associated with each other for saving and display.

CITATION LIST

Patent Document

[Patent Document 1]
  Japanese Patent Laid-Open No. 2004-361333
[Patent Document 2]
  Japanese Patent No. 4716389

SUMMARY OF THE INVENTION

Technical Problem

With the above-described circumstances in view, it is a technical object of the present invention to enable optical checks to be performed while allowing visual checks using a sample pan to be performed in a pseudo manner using an aggregate image (pseudo image) depicting grains loaded on the sample pan, by checking grains using image information imaged by an imaging apparatus such as a scanner and creating the an aggregate image using the image information.

Solution to the Technical Problem

To accomplish the object, a grain appearance measuring apparatus is provided which includes imaging means for imaging a plurality of grains, analysis means for analyzing image information on the grains imaged by the imaging means in units of grains, processing means for processing the image information to form an aggregate image of the grains, and means for saving and/or displaying the aggregate image and in which technical measures are taken such that the processing means extracts grain images from the image information in units of grains and arranges the extracted grain images in units of grains, in a close state where the grain images are close to one another (or in a densely arranged state where the images are densely arranged) to form an aggregate image of the grain images.

Technical measures are taken such that the processing means is provided with an area set value input section and such that a set value that sets a size of an area of an overlapping part of the grain images in the close state is input via the area set value input section to set an upper limit for the size of the area.

Technical measures are taken such that, when a minimum value of the set value is input to the area set value input section of the processing means, the processing means can form an aggregate image of the grain images contacting one another without any overlap.

Technical measures are taken such that the processing means provides an outer frame in the aggregate image and such that the outer frame is identical, in shape, to a grain placement surface of a sample pan.

Technical measures are taken such that a gap portion created between the grain images in the aggregate image formed by the processing means is expressed in a particular color before the aggregate image is saved and/or displayed.

Advantageous Effects of the Invention

The grain appearance measuring apparatus according to the present invention enables the appearance of each grain to be checked by means of an optical technique and enables saving or display of the aggregate image (pseudo image) depicting the checked grains loaded on the sample pan used for visual checks. This allows the results of the optical checks to be obtained, while enabling visual checks using the sample pan to be performed in a pseudo manner using the aggregate image.

The processing means of the grain appearance measuring apparatus according to the present invention sets an upper limit so as to prevent the area of the overlapping part of the grain images from being equal to or larger than a given value. This enables expression of the overlap of the grains in the same state as that in which the grains are loaded on the sample pan.

As for the aggregate image, an aggregate image can be easily created which depicts the grain images contacting one another without any overlap. The aggregate image involves no overlap of the grain images and thus enables all the images of the respective grains to be displayed.

Since the outer frame of the aggregate image is identical, in shape, to the grain placement surface of the sample pan, pseudo visual checks can be easily performed using the aggregate image.

The gap between the grains in the aggregate image is expressed in a particular color such as blue, while, black, or the like which is used for the sample pan. This allows pseudo visual checks to be easily performed using the aggregate image.

DESCRIPTION OF THE EMBODIMENTS

Figure 1:
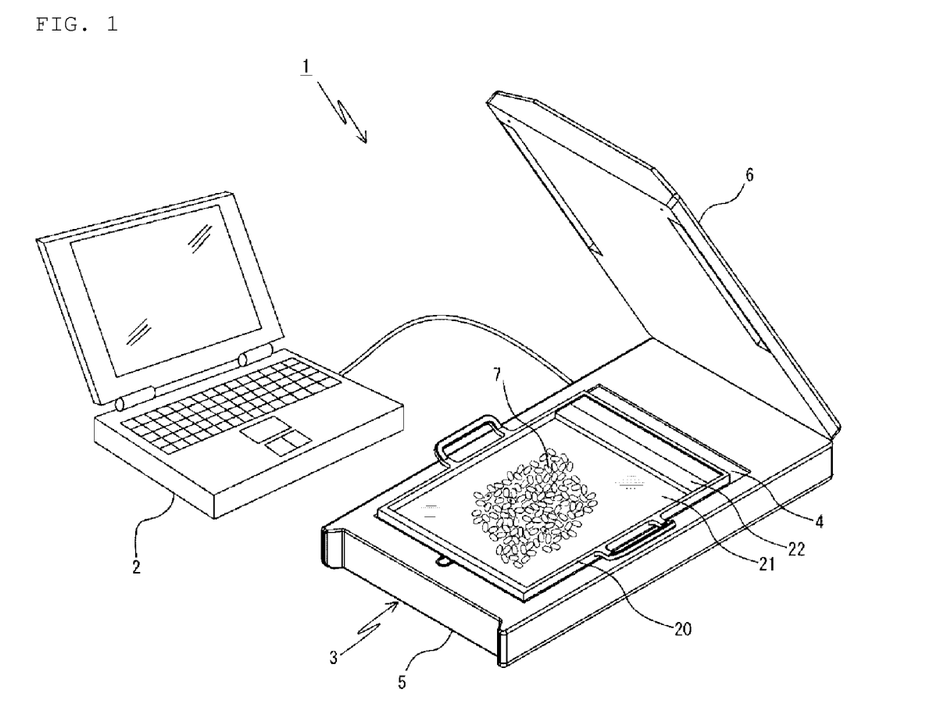
FIG. 1 is a perspective view of a grain appearance measuring apparatus according to the present invention.

The present invention will be described below in detail with reference to the drawings. FIG. 1 is a diagram depicting a grain appearance measuring apparatus 1 according to the present invention.

As depicted in FIG. 1, the grain appearance measuring apparatus 1 includes a computer 2 and a color scanner 3 connected to the computer 2 and serving as an "imaging apparatus".

The computer 2 includes analysis means for analyzing image information, processing means for processing the image information, saving means for saving the image information, display means for displaying the image information, and a function to distribute the results of measurement, the image information, or the like via a network. The computer 2 also has the functions of an area set value input section 27 described below.

The color scanner 3 includes a scanner main body 5 with an image read surface 4 on an upper end surface, and a cover 6 that covers the image read surface 4 of the scanner main body 5 during measurement.

The image read surface 4 is formed of glass and disposed on the upper surface of the scanner main body 5. The image read surface 4 is not limited to a glass plate. An acrylic plate may be used or another plate material including a transparent material may be used. A sample tray 20 is placed on the image read surface 4 during measurement.

A scanning apparatus is disposed in the scanner main body 5 and includes a light irradiating section (light source) that irradiates a bottom surface of the sample tray 20 with light and a light receiving section that receives reflected light emitted by the light irradiating section and reflected by grain surfaces.

The light receiving section of the scanning apparatus includes a color CCD and receives reflected light from grains placed on the image read surface 4, for example, for each of three colors of RGB (Red, Green, and Blue). The light receiving section outputs the image information obtained by the light reception to the computer 2.

The cover 6 is hinged at one side thereof to an upper end side of the scanner main body 5 and can be pivoted via the hinge. During measurement, the cover 6 can cover the image read surface 4 of the scanner main body 5, allowing external stray light to be prevented. A common scanner may be used as the color scanner 3.

The sample tray 20 of the grain appearance measuring apparatus 1 according to the present embodiment will be described. As depicted in the figures, the sample tray 20 is formed like a rectangular frame as seen in plan view and includes a bottom plate 21, a sidewall extending upward from a peripheral portion of the bottom plate 21, and gripping portions provided at two positions on the sidewall for easy handling. The bottom plate 21 is a transparent plate, and an acrylic resin or the like used for the bottom plate 21. With the sample tray 20 placed on the upper surface of the image read surface 4, the bottom surface 21 is placed in abutting contact with the upper surface of the image read surface 4.

A reference plate 22 may be provided in a part of an area enclosed by the sidewall. The reference plate 22 allows acquisition of image information used to correct measured values from the color scanner 3. A position where the reference plate 22 is disposed is not particularly limited if it is within the area but may be any position that is convenient for design. Furthermore, the shape of the reference plate 22 is also not particularly limited, but a rectangular shape facilitates design. In the present embodiment, the reference plate 22 is shaped like a rectangle, and located in contact, at a longitudinal end of the reference plate 22, to the sidewall. The reference plate 22 may be formed so as to have only one color. However, two colors of reference plates, for example, a white reference plate and a black reference plate, are desirably combined together.

Measurement is performed on the sample tray 20 using the color scanner 3, and thus, reflected light from the sample tray 20 main body is expected to exert an adverse effect during the measurement. To prevent the adverse effect of the reflected light, at least the surface of the sample tray 20 is preferably matte. The sample tray 20 is desirably formed of a blackbody or a material similar to a blackbody.

Operations and effects of the present embodiment will be described. In the present embodiment, a case will be described in which grains to be checked are brown rice grains.

About 1,000 brown rice grains 7 are loaded on the bottom surface 21 of the sample tray 20 so as not to lie on top of one another. After the loading, the sample tray 20 is placed on the image read surface 4 of the color scanner 3 as depicted in FIG. 1. During measurement using the color scanner 3, the bottom surface 21 of the sample tray 20 serves as an optical path, and thus, staining of the bottom surface 21 resulting from contact with the finger or the like is not preferable. The number of grains measured during a single measurement operation is not particularly limited but may be increased or reduced so as not to exceed the number of grains that can be placed on the bottom surface of the sample tray.

After the sample tray 20 is placed, a top surface of the sample tray 20 is covered with the cover 6, and an image of the brown rice grains 7 is imaged using the color scanner 3. In a specific imaging operation, the scanning apparatus in the scanner main body 5 is moved along the bottom surface of the image read surface 4 (two-dimensional scan). At this time, the light irradiating section of the scanning apparatus irradiates the brown rice grains 7 with light. Reflected light from the brown rice grains 7 is received by the light receiving section of the scanning apparatus. The optically received signal is output to the computer 2 as RGB image information. For the brown rice grains 7 imaged by the color scanner 3, a lower side of each grain, that is, a surface coming into contact with the bottom surface 21, is imaged.

Figure 11:
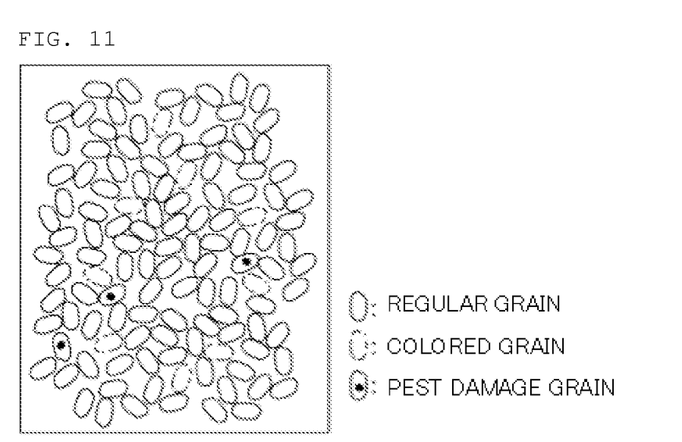
FIG. 11 is image information on grains imaged by the grain appearance measuring apparatus according to the present invention.

Analysis of the image information using the computer 2 allows the appearance of the measured brown rice grains (whole grain, crushed rice, dead rice, colored rice, blue immature rice, pest damage rice, and the like) to be optically accurately checked and sorted. The computer 2 can save and display the image information. FIG. 11 depicts an example of a case where the image information is displayed by the computer 2.

The analysis performed by the computer 2 may use a general analysis method. For example, such a method as described in Japanese Patent Laid-Open No. 2011-242284 may be used. Furthermore, in the present embodiment, the brown rice grains are measured without being brought into lines. However, for example, each brown rice grain can be identified in units of grains by means of such image processing as described in CN101281112 (unexamined patent publication) laid open in China. Thus, as depicted in FIG. 12, images of the measured brown rice grains 7 can also be displayed such that the brown rice grains are brought into lines in units of grains.

Figure 2:
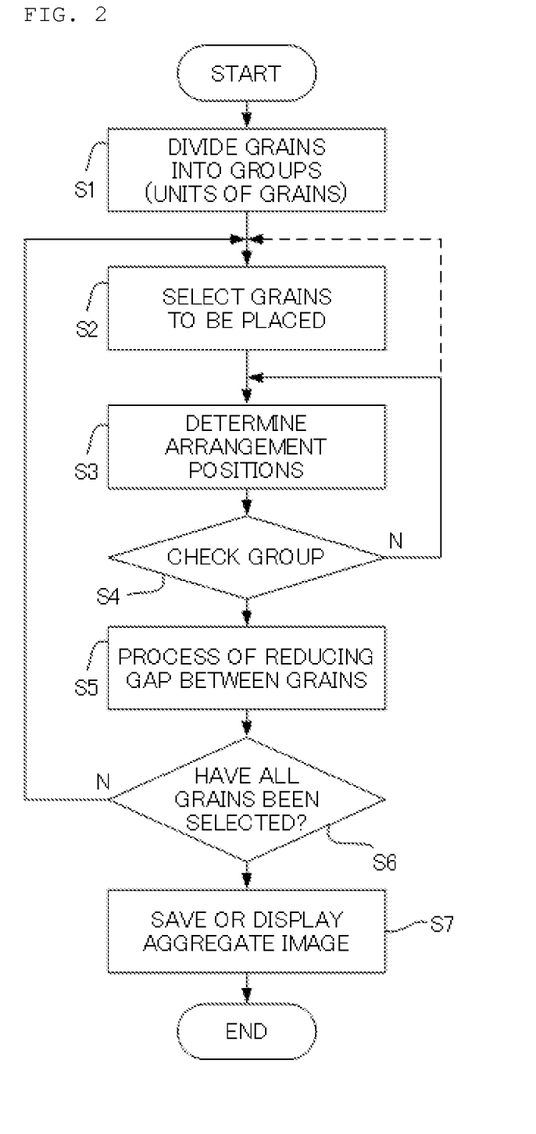
FIG. 2 is a flowchart depicting a procedure for creating an aggregate image according to the present invention.

A method will be described in which an aggregate image (pseudo image) of the grains loaded on the sample pan is created using the image information. FIG. 2 is a flowchart depicting a procedure for creating an aggregate image.

First, the processing means of the computer 2 groups the measured grains in units of grains (step S1). The grouping may be performed according to the appearance of each grain such as whole grain, colored grain, blue immature grain, pest damage grain, crushed grain, and the like. In the present embodiment, for facilitation of description, a case will be described where the grains are divided into three groups, a group of whole grains, a group of colored grains, and a group of pest damage grains. A method for the grouping is not particularly limited. The measured grains may be divided into 256 levels according to the color of the grain before the grains are divided into a plurality of groups.

To allow the grain images grouped in step S1 to be arranged in order inside an outer frame 25 of an aggregate image to be created, the images of grains to be arranged are selected (step S2). For selection of the grain images, the grain images in the image information extracted in units of grains may be selected in order one by one. For example, in the image information depicted in FIG. 12, the images may be selected in order starting with the upper left image in FIG. 12. The image of one grain is selected only once. The outer frame 25 of the aggregate image is preferably identical, in shape, to a grain placement surface (bottom surface) of the sample pan. The outer frame 25 is normally round but may be freely set to be, for example, rectangular. In the present embodiment, the outer frame 25 is round.

The outer frame 25 may be identical, in size, to the grain placement surface of the actual sample pan. However, the outer frame 25 may be reduced in size, and in that case, the grain images need to be subjected to the same size reduction to which the outer frame 25 is subjected.

Figure 3:
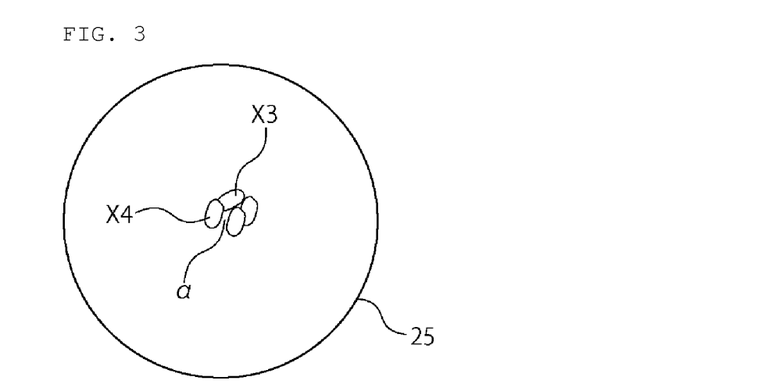
FIG. 3 is a diagram depicting a method for creating an aggregate image according to the present invention.

Now, step S3 will be described which involves determining the positions (coordinates) where the grain images selected in step S2 are arranged. FIG. 3 depicts an aggregate image at an initial stage of creation. The image of the first (first) grain selected first may be freely placed inside the outer frame 25. The images of the second and subsequently selected grains are placed at least partly adjacent to the already placed grain image. At this time, the angles of the grains on the image may be freely set. FIG. 3 depicts a stage where a fourth grain image X4 is placed inside the outer frame 25. The grain image X4 is an image of a whole grain and is placed adjacently to the already placed grain image X3 so as to partly and slightly overlap the grain image X3. The term "adjacent" for the grain images according to the present invention includes a state in which the grain images partly overlap each other.

After the grain image X4 is placed, a group of the grains to which the grain image X4 is adjacent is checked. An object of the present invention is to reproduce, in a pseudo manner, an image of grains loaded on the sample pan during visual checks. Thus, the grains other than the whole grains, that is, colored grains and pest damage grains, need to be arranged dispersedly inside the aggregate image. Thus, a group of placed grain images to which a grain image to be newly placed is placed adjacently is checked at the placement in step S3 in order to allow whole grains to be arranged in contact with each other, while avoiding the arrangement in which colored grains contact each other, in which pest damage grains contact each other, or in which a colored grain and a pest damage grain contact each other (step S4). In FIG. 3, the grain image X4 corresponds to a whole grain that may be adjacent to any grains, that is, a whole grain, a colored grain, and a pest damage grain. The grain image X4 may be placed at this position without posing a problem. The present embodiment separately provides step S3 and step S4, but the check of the group may be performed at the time of step S3.

Figure 5:
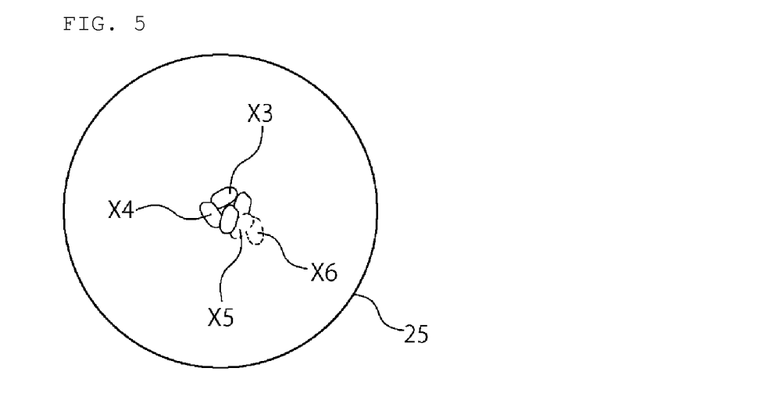
FIG. 5 is a diagram depicting the method for creating an aggregate image according to the present invention.
Figure 6:
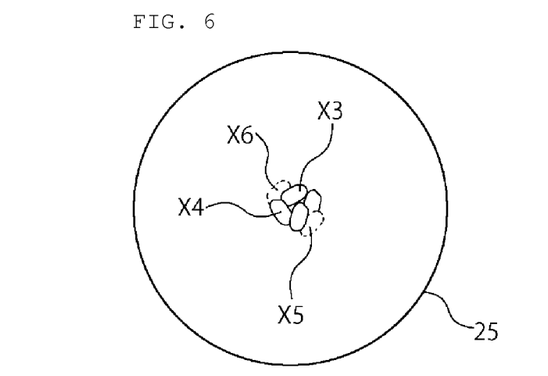
FIG. 6 is a diagram depicting the method for creating an aggregate image according to the present invention.

Step S4 (check of the group) will be described using FIG. 5 and FIG. 6. FIG. 5 depicts that a sixth grain (colored grain) image X6 is placed adjacently to a fifth grain (colored grain) image X5. In this case, the colored grains are adjacent to each other, and thus, the position (coordinates) where the grain image X6 is placed is changed so that the grain image X6 is repositioned adjacently to another grain image or the sixth placement of the grain image X6 is halted and an image of another grain (in this case, a whole grain) is selected from the image information (step S2). FIG. 6 depicts a case where the position where the grain image X6 is placed has been changed. The position where the grain image X6 is placed has been changed to a position where the grain image X6 is adjacent to grain images X3 and X4 corresponding to whole grains. This avoids arranging colored grains adjacently to each other.

During the placement in the step S3, the following operation needs to be performed. Whether the area in which a newly placed grain image overlaps another placed grain image exceeds a preset set value is checked. When the area of the overlap is determined to exceed the set value, the positions of the corresponding grain images need to be adjusted in order to avoid the overlap. At this time, the positions of one or both of the grain image to be newly placed and the already placed grain image are adjusted.

The set value may be set in terms of the size of the area of the overlapping part of two grain images. However, in the present embodiment, the set value is set in terms of the "rate" of the area of the overlapping part of the two grain images with respect to the area of the entire images. The rate is determined by "the area of the overlapping part of grains/the total area of the grain images". The value of the rate is set to be 25% as a set value. Thus, the size of the area of the overlapping part of grain images is allowed to be up to 25% of the total area of the grain images. The set value is input via the area set value input section 27 provided with the computer 2.

The size of the grain varies among the grains, and thus, the size of the grain image varies among the images. Thus, even when the area in which a grain image Y1 to be newly placed overlaps a placed grain image Y2 is equal to or smaller than the set value (rate), if the placed grain image Y2 is smaller than the grain image Y1 to be newly placed, for the grain image Y2, the rate of the area in which the grain image Y2 overlaps the grain image Y1 may exceed the set value. Hence, even for already placed grain images, the area in which the placed grain image overlaps a grain image to be newly placed needs to be prevented from exceeding the set value. Even for already placed grain images, the following operation needs to be performed. The size or rate of the area in which the already placed grain image overlaps a grain image to be newly placed is determined. Whether the size or rate exceeds the set value is checked. When the size or rate exceeds the set value, the position of the grain image to be newly placed or the placed grain image overlapping the grain image to be newly placed needs to be adjusted. For placed grain images, an aggregate image may be created with the overlapping part of the placed grain image and a grain image to be newly placed neglected, or the position adjustment may be omitted even when an overlap exceeding the set value occurs only on the already placed grain image side.

During the placement in the step S3, the rate of the area in which the grain image to be newly placed overlaps the already placed grain image, with respect to the area of the grain image to be newly placed, or the rate of the area in which the already placed grain image overlaps the grain image to be newly placed, with respect to the area of the already placed grain image, need not be all 25%. The rate may be freely set to 25% or less for each grain. Set values at a plurality of stages between 0% and 25% may be provided such that, for each grain, the size of the overlap can be determined to have any of the set values. Preferably, as the set values, six set values of 0%, 5%, 10%, 15%, 20%, and 25% are provided, and during the placement in step S3, any of the set values is selected for each grain so that grain images are reproduced on an aggregate image based on a plurality of types of manners of overlapping. The upper limit on the set value is not necessarily limited to 25% but may be determined to have any value according to the purpose of the aggregate image to be created. The range of the set value is also not necessarily limited to 5%, but may be set to have any value of range as appropriate according to the purpose of the aggregate image to be created. For a set value of 0%, grain images contact each other without any overlap.

During the placement in step S3, a part of a grain image may stick out from the outer frame 25. That case is dealt with by setting, as a set value, the size or rate of the area of a part of the grain image which is allowed to stick out from the outer frame 25. The set value in that case may be set as the size or rate of the area of a part of the grain image which sticks out from the outer frame 25. The rate of the area in the corresponding grain may be determined to be "the area of the part of the grain image which sticks out from the outer frame 25/the total area of the grain image". In the present embodiment, the set value is 25% of the rate. Thus, even when a part of the grain image sticks out from the outer frame 25, the rate is allowed to be up to 25%. The set value is not necessarily limited to 25% but may be changed as appropriate according to the purpose of the aggregate image to be created. As is the case with the overlap of grain images, set values may be provided at a plurality of stages such that the area of the part of the grain image which sticks out from the outer frame 25 may be set to any magnitude. For a set value of 0%, no part of the grain image is displayed outside the outer frame 25, and the outermost edge of the image contacts the outer frame 25.

When grain images are laid on top of each other, one of the grain images is positioned above or below the other grain image. When a plurality of grain images are laid on top of each other, the vertical relation of the grain images, that is, which of the grain images is positioned above or below the other grain image, needs to be determined. However, the vertical relation may be optionally and freely determined. The vertical relation may be determined based on a particular rule.

Figure 4:
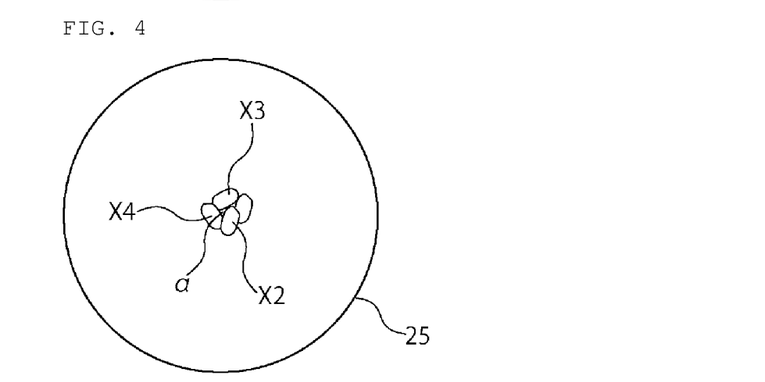
FIG. 4 is a diagram depicting the method for creating an aggregate image according to the present invention.

After step S4, the positions (coordinates) of the grain images are adjusted as needed. In this position adjustment, a process of reducing a gap α depicted in FIG. 3 is executed (step S5). Specifically, as depicted in FIG. 4, the gap α is reduced by rotating the grain image X4 with the adjacency between the grain image X4 and the grain image X3 maintained to adjust the position of the grain image X4 so that the grain image X4 is also adjacent to another grain image X2. Visual checks of grains are performed with the grains densely arranged on the sample pan without any gap. Thus, the process of reducing the gap in step S5 is needed in order to express the densely arranged grains in the aggregate image to be created.

In the process of reducing the gap in step S5, one grain image is adjacent to a plurality of grain images (except during the initial stage of creation of the aggregate image). Thus, the size or rate of the area of the overlapping part needs to be determined for each of the adjacent grain images. The size or rate may be determined by providing a set value based on the size or rate of the area of the overlapping part of the grain images as is the case with step S3. In the present embodiment, the rate in the corresponding grain image is determined to be "the area of the overlapping part of the grains/the total area of the grain image". The set value in step S3 and the set value in step S5 may be common or may be individual values that are managed. The set value in step S5 is also input via the area set value input section 27 of the computer 2.

As is the case with step S3, in step S5, even when the area in which a grain image Z1 to be newly placed overlaps a placed grain image Z2 is equal to or smaller than the set value (rate), if the placed grain image Z2 is smaller than the grain image Z1 to be newly placed, for the grain image Z2, the rate of the area in which the grain image Z2 overlaps the grain Z1 may exceed the set value. Hence, even for already placed grain images, the area in which the placed grain image overlaps a grain image to be newly placed needs to be prevented from exceeding the set value.

Even for already placed grain images, the following operation needs to be performed. The size or rate of the area in which the already placed grain image overlaps a grain image to be newly placed is determined. Whether the size or rate exceeds the set value is checked. When the size or rate exceeds the set value, the position of the grain image to be newly placed or the placed grain image overlapping the grain image to be newly placed is adjusted. For placed grain images, an aggregate image may be created with the overlapping part of the placed grain image and a grain image to be newly placed neglected, or the position adjustment may be omitted even when an overlap exceeding the set value occurs only on the already placed grain image side.

In the present embodiment, the value of the rate in step S5 is set to 25% as a set value. Thus, the area of the overlapping part of grain images is allowed to be up to 25% of the total area of the grain images. In step S5, the areas in which the grain image to undergo position adjustment overlaps the already placed grain images need not be all 25%. The rate may be freely set to 25% or less for each grain. Furthermore, it is preferable that set values at a plurality of stages between 0% and 25% be provided such that, for each grain, the size of the overlap can be determined to have any of the set values. For example, as the set value, six set values of 0%, 5%, 10%, 15%, 20%, and 25% are provided, and that during the position adjustment in step S5, any of the set values is selected so that grain images are reproduced on an aggregate image based on a plurality of types of manners of overlapping. The upper limit on the set value is not necessarily limited to 25% but may be determined to have any value of range as appropriate according to the purpose of the aggregate image to be created. The range of the set value is also not necessarily limited to 5%, but may be set to have any value according to the purpose of the aggregate image to be created. For a set value of 0%, grain images contact each other without any overlap.

Figure 9:
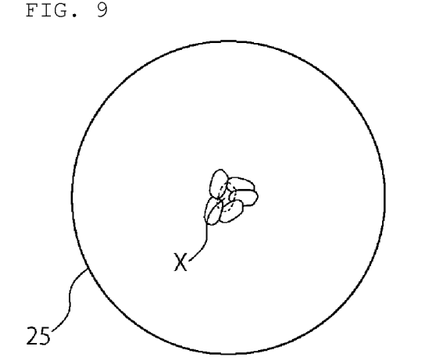
FIG. 9 is a diagram depicting a method for creating an aggregate image according to the present invention.

As depicted in FIG. 9, when a certain grain image X (depicted by a dotted line) overlaps a plurality of grain images during the position adjustment in step S5, the grain image X overlaps the respective grain images at any individual rates. In this case, the rate of the total area in which the grain image X overlaps all the adjacent grain images, with respect to the area of the grain image X, may exceed 50%. Thus, during the position adjustment in step S5, a set value is preferably provided so as to prevent the rate of the total area in which the grain image to undergo position adjustment overlaps other grain images, with respect to the area of the target grain image, from exceeding a given value, in turn preventing a possible overlap exceeding the set value. When grain images overlap each other, the upper overlapping image is displayed in the aggregate image. Thus, when the rate is determined, the area of the upper overlapping portion may be excluded from the calculation of the total area.

Figure 7:
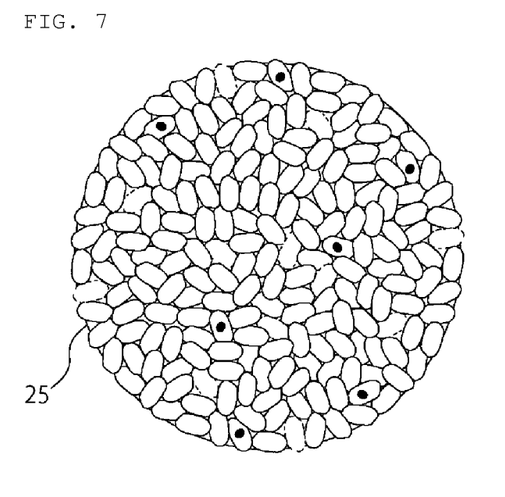
FIG. 7 is a diagram depicting an example of an aggregate image according to the present invention.
Figure 8:
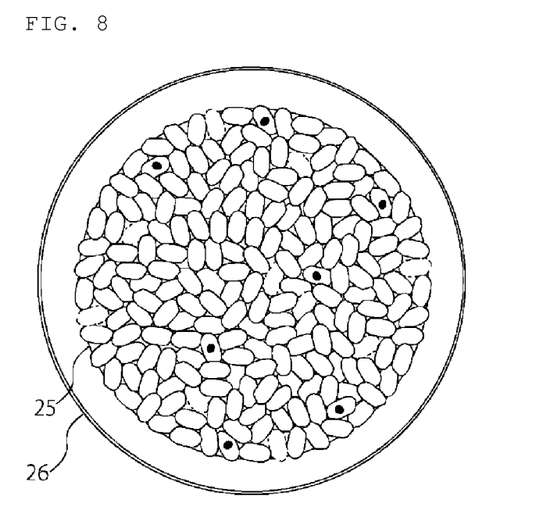
FIG. 8 is a diagram depicting an example of the aggregate image according to the present invention.

The operations up to step S5 are repeatedly performed until all the grain images in the image information are placed in the aggregate image. After all the grain images are placed, the created aggregate image is saved and/or displayed. FIG. 7 is a diagram depicting the created aggregate image. As depicted in FIG. 8, an image using a plan view of the sample pan 26 may be created as a background of the aggregate image and saved and/or displayed. When the created aggregate image is not only displayed on the computer 2 but also allowed to be browsed using the Internet, the created aggregate image may be utilized on site during trade of grains even in a remote place such as a foreign country.

Figure 10:
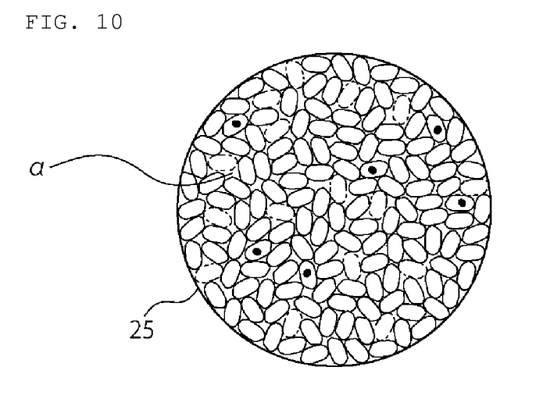
FIG. 10 is a diagram depicting an example of the aggregate image according to the present invention.

FIG. 10 is an aggregate image of grain images contacting one another without any overlap. In the present invention, the aggregate image can be easily created by minimizing the set value of the size or rate of the overlap of the grain images (0 or 0%).

During the final stage of creation of the aggregate image, when a space fails to be secured which allows a grain image of one or more grains to be placed in the outer frame 25, those grain images need not be forcibly placed and the image obtained at that point in time may be the final aggregate image.

The gap α may be displayed or saved in any color but may preferably be in the same color as the color of the sample pan and may be blue, black, white, or the like. The gap α serves as a background in the aggregate image, and thus, a color that facilitates checks may be freely selected for each grain to be checked.

In the above-described embodiment, the arrangement is set so as to prevent colored grains from contacting each other, to prevent pest damage grains from contacting each other, or to prevent a colored grain and a pest damage grain from contacting each other. However, step S1 and step S4 may be omitted to create an aggregate image in which colored grains may contact each other, in which pest damage grains may contact each other, or in which a colored grain and a pest damage grain contact each other.

An apparatus may be used as an imaging apparatus according to the present invention provided that grain images can be acquired in units of grains. The present invention can be implemented in an apparatus that conveys and images grains grain by grain, for example, as described in Japanese Patent Laid-Open No. 2006-200945.

INDUSTRIAL APPLICABILITY

The grain appearance measuring apparatus according to the present invention enables not only grains but also beans to be checked. Furthermore, the grain appearance measuring apparatus according to the present invention may be used for checking granular objects such as resin pellets.

LIST OF REFERENCE SIGNS LIST

1 Grain appearance measuring apparatus
2 Computer
3 Color scanner
4 Image read surface
5 Scanner main body
6 Cover
7 Brown rice grain
20 Sample tray
21 Bottom surface
22 Reference plate
25 Outer frame

The invention claimed is:

1. A grain appearance measuring apparatus comprising:
a scanner for imaging a plurality of grains; and
a computer configured to:
analyze image information on the grains imaged by the scanner in units of grains;
process the image information to form an aggregate image of the grains; and
save and/or display the aggregate image,
wherein the computer extracts grain images from the image information in units of grains and arranges the extracted grain images in units of grains, in a close state where the grain images are close to one another and/or partly overlap to form an aggregate image of the grain images, and saves and/or displays an image of the aggregate image of the grains on a sample pan.

2. The grain appearance measuring apparatus according to claim 1, wherein the computer is provided with an area set value input section, and
a set value that sets a size of an area of an overlapping part of the grain images in the close state is input via the area set value input section.

3. The grain appearance measuring apparatus according to claim 2, wherein, when a minimum value of the set value is input to the area set value input section, the computer forms an aggregate image of the grain images contacting one another without any overlap.

4. The grain appearance measuring apparatus according to claim 1, wherein the computer provides the aggregate image with an outer frame that is identical, in shape, to a grain placement surface of a sample pan.

5. The grain appearance measuring apparatus according to claim 1, wherein a gap portion created between the grain images in the aggregate image formed by the processing is expressed in a particular color before the aggregate image is saved and/or displayed.

\* \* \* \* \*